United States Patent [19]
Guo

[11] Patent Number: 5,967,967
[45] Date of Patent: Oct. 19, 1999

[54] HEALTH COMB

[76] Inventor: Liwen Guo, No. 169 Tongxiang St. Dongli District, Harbin, China

[21] Appl. No.: 08/934,462

[22] Filed: Sep. 19, 1997

[30] Foreign Application Priority Data

Dec. 13, 1996 [CN] China .................................. 96120547

[51] Int. Cl.⁶ .............................. A61B 17/52; A61N 1/26; A61N 2/00
[52] U.S. Cl. .................................. 600/9; 600/13; 607/79
[58] Field of Search .................................. 607/1, 79, 115, 607/145, 148, 149, 150, 152; 600/9, 11, 13, 14, 15

[56] References Cited

U.S. PATENT DOCUMENTS

| | | | |
|---|---|---|---|
| 751,839 | 2/1904 | Doersch | 607/79 |
| 1,052,522 | 2/1913 | Sence | 607/79 |
| 1,532,463 | 4/1925 | Winterfield | 607/79 |

*Primary Examiner*—Samuel Gilbert
*Attorney, Agent, or Firm*—Adams & Wilks

[57] ABSTRACT

A health comb for therapeutic treatment of the body of a user comprises a comb body and serially connected electrically conductive teeth elements supported by the comb body. At least one electrode is supported by the comb body and is connected to the electrically conductive teeth elements. An electromagnetic device is connected to the electrically conductive teeth elements for generating an electromotive force to produce an electric current and for directing magnetic field flux energy to a to-be-treated area of the health comb user's body. A semiconductor circuit is connected to the electromagnetic device and to the electrically conductive teeth elements for controlling flow of electric current from the electrically conductive teeth elements to the electrode.

31 Claims, 3 Drawing Sheets

HEALTH COMB

BACKGROUND OF THE INVENTION

1. Field of the Invention

The present invention relates to an instrument for physical therapy in the field of health care and, more particularly, to a health comb for therapeutic treatment having a semiconductor circuit and an electromagnetic device.

2. Background Information

The intensified work and study with quick rhythm in modern life imposes some pressure upon the human spirit and mentality, giving rise to an obstruction in the biological circulation of the human body and causing headache, dizziness, high blood pressure and insufficient supply of blood to the brain. It is shown by medical studies that, when the above symptoms appear, the biological electric level at concentrated parts of the human head is much higher than at the ends of nerves.

Chinese Utility Model No. 92207517.4 discloses a type of comb for vitalizing the brain and lowering down blood pressure. The comb disclosed in the Chinese Utility Model includes a comb body, comb teeth, wires, a circuit board and a hand electrode. The comb teeth are arranged into a line, and when combing hair, the biological electricity at the acupuncture points on the top of the head is conducted via the comb teeth to the circuit board and then in turn transmitted to the hand electrode. Through the hand, the electricity is transmitted into the human body so as to offset the difference of electric levels of the biological electricity at the acupuncture points on the top of the head and that within the human body, so that the goals of enlivening the brain and lowering down blood pressure are achieved. However, since the foregoing comb does not have a magnetic apparatus, the results of enlivening the brain and lowering down blood pressure by balancing the biological electricity within the human body is not satisfactory.

One of the objectives of the present invention is to provide a health comb which may automatically, at the same time of combing hair, adjust the biological electric levels of various portions of the human body, thereby maintaining balance of the biological electricity of the human body.

Another of the objectives of the present invention is to provide a health comb which may at the time of combing hair apply magnetic medical treatment to the head.

SUMMARY OF THE INVENTION

The foregoing and other objects of the present invention are accomplished by providing a health comb comprising a comb body, a plurality of serially connected electrically conductive teeth elements supported by the comb body, and at least one touch electrode supported by the comb body and connected to the electrically conductive teeth elements. An electromagnetic device is connected to the electrically conductive teeth elements for generating an electromotive force to produce an electric current and for directing magnetic field flux energy to a to-be-treated area of the health comb user's body. A semiconductor circuit is connected to the electromagnetic device and to the electrically conductive teeth elements for controlling flow of electric current from the electrically conductive teeth elements to the electrode.

A wire having first and second opposite connecting ends connects the electrically conductive teeth elements in series. Preferably, each of the electrically conductive teeth elements is formed of metal and has a surface coated with silver for enhancing the electrical conductivity.

The comb body preferably comprises a first portion, a second portion integral with the first portion and a cover portion integrally connected with the second portion to define a handle portion of the comb body. A base member formed of insulation material is integrally connected to the first portion of the comb body for supporting the electrically conductive teeth elements.

According to the present invention, the at least one electrode comprises two electrodes supported by the comb body and connected to the electrically conductive teeth elements. One of the electrodes comprises a hand-touch electrode which is touched by a hand of the user during use of the health comb, and the other of the electrodes comprises a foot-touch electrode which is touched by a foot of the user during use of the health comb. Preferably, the electrically conductive teeth elements, the hand-touch electrode, the foot-touch electrode, the electromagnetic device and the semiconductor circuit are connected in series.

The health comb comprises connecting means for releasably electrically connecting the foot-touch electrode to the semiconductor circuit. Preferably, the connecting means comprises an electrical socket integral with the handle portion of the comb body and electrically connected to the semiconductor circuit, and an electrical plug integral with the foot-touch electrode for releasable electrical connection to the electrical socket.

Preferably, the semiconductor circuit comprises a crystal diode circuit. The diode circuit has first and second diodes for controlling a flow of the electric current from the electrically conductive teeth elements to the hand-touch electrode and the foot-touch electrode. The first diode has an anode connected to the first connecting end of the wire and has a cathode connected to the foot-touch electrode. The second diode has an anode connected to the second connecting end of the wire via the electromagnetic device and has a cathode connected to the hand-touch electrode. The semiconductor circuit also has a pair of resistors each respectively connected in parallel with the diodes for improving the linear characteristics of the circuit.

The electromagnetic device preferably comprises an inductive coil and a permanent magnet. The inductive coil has one end connected to the anode of the second diode and another end connected to the second connecting end of the wire.

The semiconductor circuit, the electromagnetic device and the touch electrodes of the health comb of the present invention form, jointly with the human body, a circulation system of biological electricity outside of the human body, whereby the biological electric level at various parts of human body may be adjusted, the biological circulation may be improved, and some symptoms caused by a hindered human circulation system, such as high blood pressure, dizziness, headache, memory failure, insufficient supply of blood to brain, insomnia, amnesia and hair-falling may be relieved. In addition, the health comb of the present invention functions to apply magnetic treatment to the user's head.

BRIEF DESCRIPTION OF THE DRAWINGS

An embodiment of the health comb according to the present invention is illustrated with reference to the accompanying drawings in which.

DETAILED DESCRIPTION OF THE PREFERRED EMBODIMENTS

Figure 1:
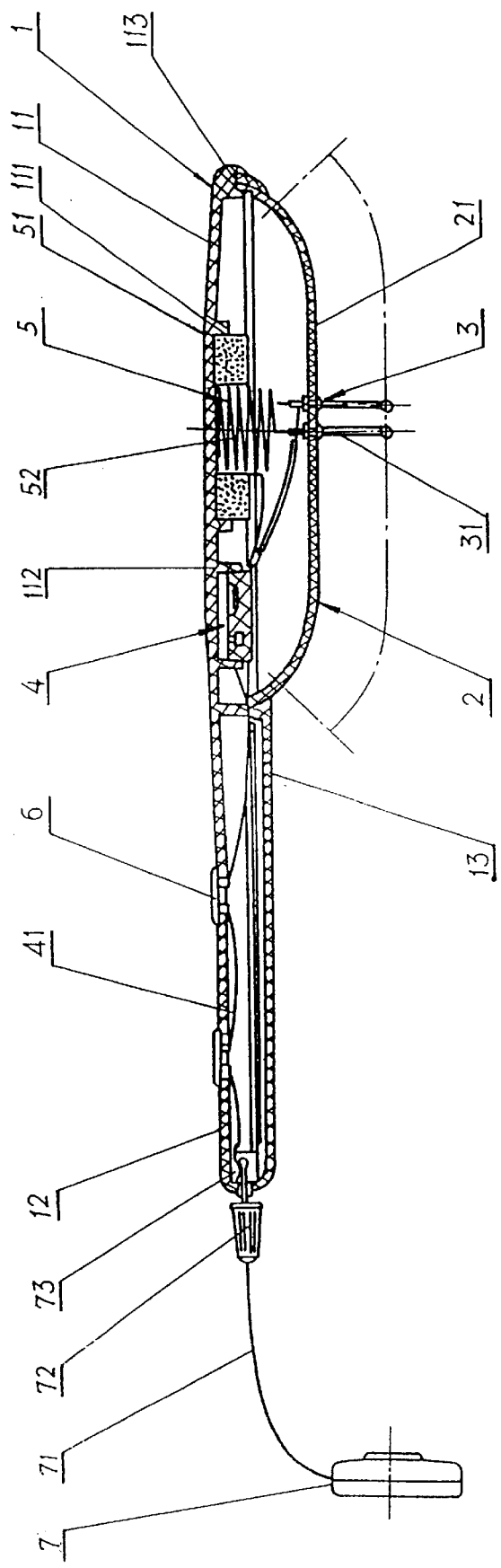
FIG. 1 is a partial cross-sectional view of the structure of the health comb according an embodiment of the present invention.
Figure 2:
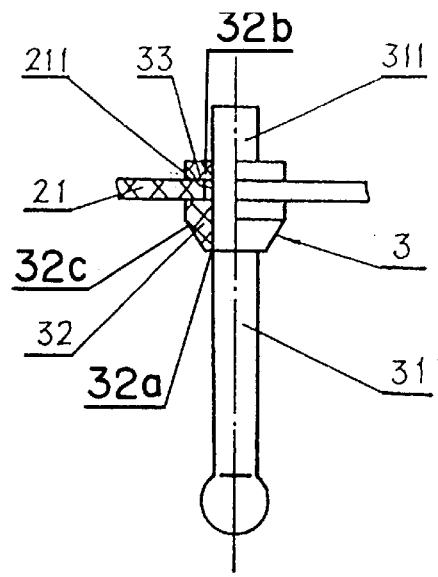
FIG. 2 is a structural view of one of the electrically conductive comb teeth elements of the embodiment of the health comb according to the present invention.

Referring to FIGS. 1 and 2, the health comb comprises a comb body 1, a plurality of serially connected electrically conductive teeth elements 3 supported by the comb body, and electrodes 6, 7 supported by the comb body and connected to the electrically conductive teeth elements. An electromagnetic device 5 is connected to the electrically conductive teeth elements 3 for generating an electromotive force to produce an electric current and for directing magnetic field flux energy to a to-be-treated area of the health comb user's body. A semiconductor circuit 4 is connected to the electromagnetic device 5 and to the electrically conductive teeth elements 3 for controlling flow of electric current from the electrically conductive teeth elements to the electrodes 6.

The comb body 1 has a first portion or comb casing 11 at a front end thereof, a second portion 12 at a rear end thereof and integral with the comb casing 11, and a cover portion 13 integrally connected with the second portion 12 to define a handle portion of the comb body. The comb casing 11 has an inner surface provided with a pair of first support portions 111 and a second support portion 112, and has an inlaid groove 113 at a front end portion thereof. The comb body 1, including the comb casing 11, the second portion 12 and the cover portion 13, are preferably formed of a plastic material. The semiconductor circuit 4 is fixedly supported by the second support portion 112 of the comb casing 11. The electromagnetic device 5 is fixedly supported by the first support portions 111 of the comb casing 11.

According to the present invention, the electrodes 6 comprise hand-touch electrodes which are disposed on the second portion 12 of the comb body 1 and which are touched by a hand of the user during use of the health comb. The electrode 7 comprises a foot-touch electrode which is touched by a foot of the user during use of the health comb. The foot-touch electrode 7 is electrically connected to the semiconductor circuit 4 by means of a wire 71 and an electrical plug 72 connected to an electrical socket 73 integral with the comb body 1. The hand-touch electrodes 6 and the foot-touch electrode 7 are preferably formed of materials having good electrical conductivity.

Preferably, the electrically conductive teeth elements 3, the touch electrodes 6, 7, the electromagnetic device 5 and the semiconductor circuit 4 are connected in series.

A base member or fixing board 2 is integrally connected to the comb casing 11 for supporting the electrically conductive teeth elements 3. The fixing board 2 has a generally bowl-shaped hollow body having an inlaid rim fixed into the inlaid groove 113 of the comb casing 11. A bottom surface 21 of the fixing board 2 has openings 211 through which respective electrically conductive teeth elements 3 extend and in which they are fixed. Preferably, the fixing board 2 is made of a soft insulation material, such as rubber board.

As shown in FIG. 2, each of the electrically conductive teeth elements 3 comprise a comb teeth 31 and a base 32 having holes 32a for respectively receiving and supporting the comb teeth 31. The base 32 has a generally column-shaped upper portion 32b and a generally cone-shaped lower portion 32c. The upper portion 32b of the base 32 has a groove 33 receiving a rim portion of one of the openings 211 formed on the bottom surface 21 of the fixing board 2 for firmly fixing the electrically conductive teeth elements 3 on the bottom surface 21 of the fixing board 2. Each of the comb teeth 31 has an end defining an electrode portion 311. Alternatively, the comb teeth 31 may be formed unitarily with the fixing board 2 by a plastic molding or glue-binding process.

The comb teeth 31 are made of metal and the surface thereof may be coated with silver so as to enhance the electrical conduction.

Figure 3:
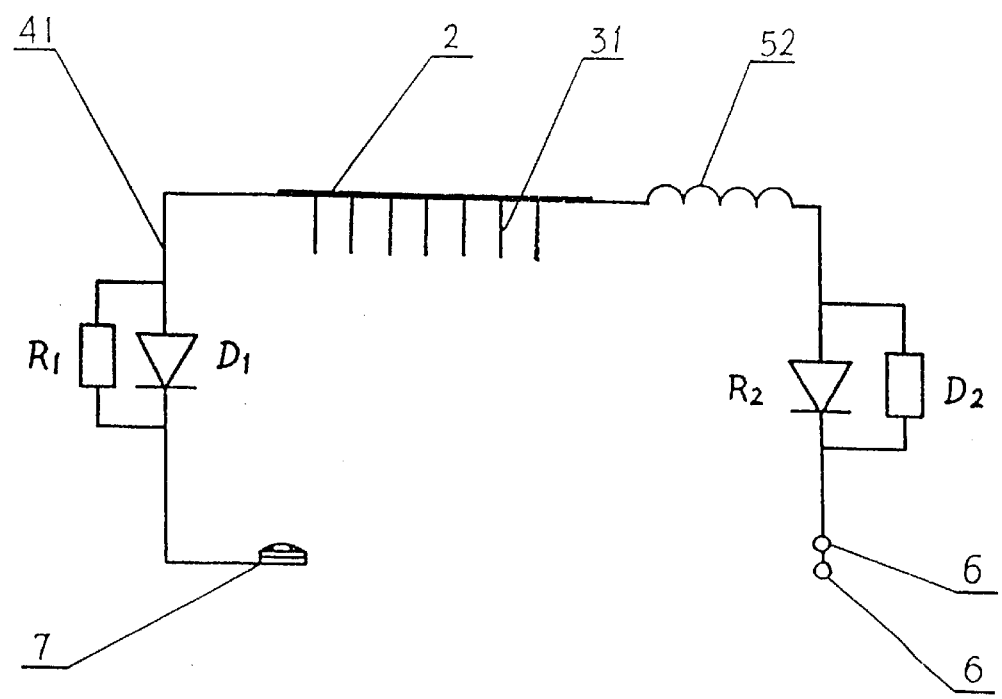
FIG. 3 is a circuit diagram of the embodiment of the health comb according to the embodiment of the present invention.
Figure 4:
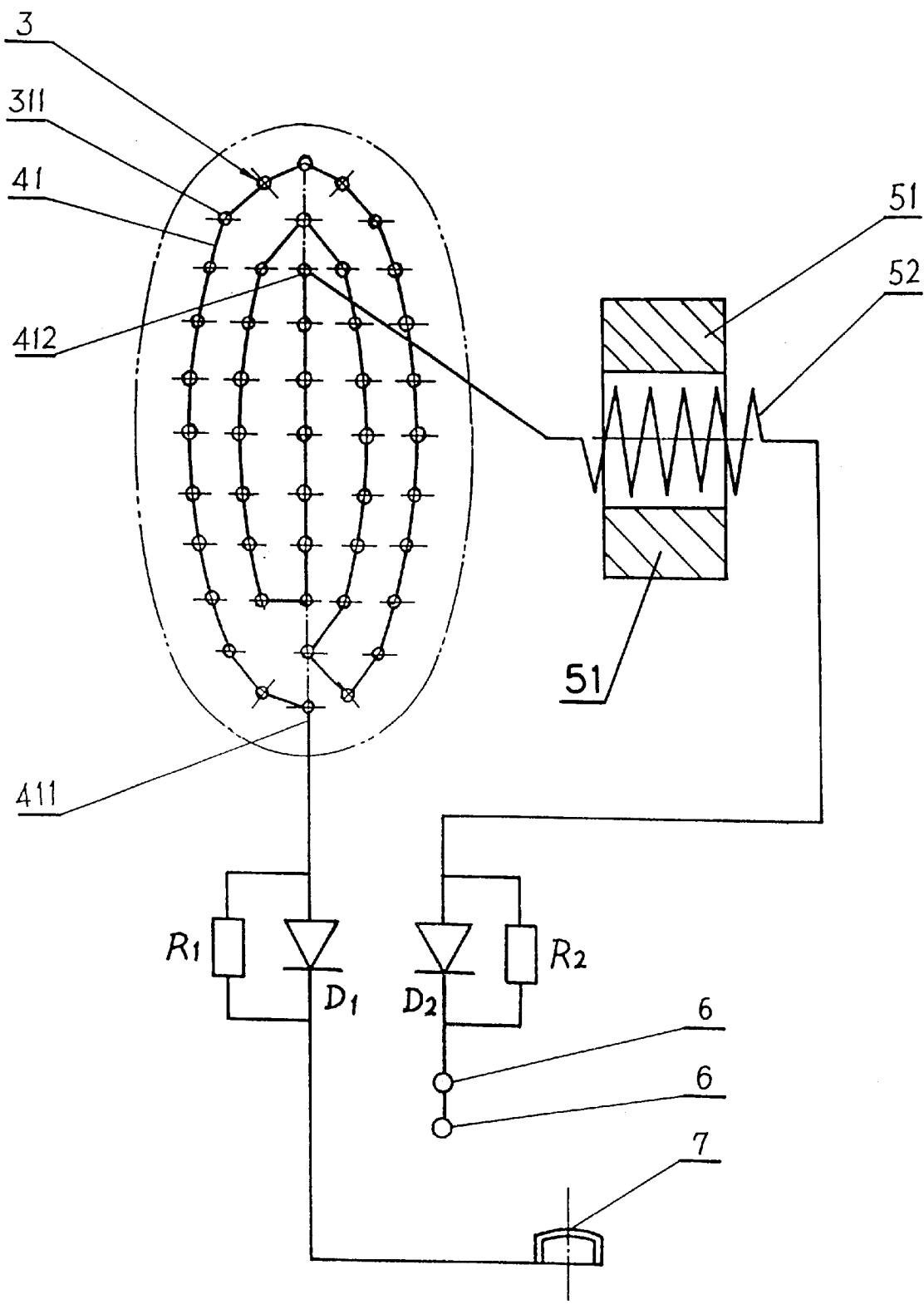
FIG. 4 is a schematic of the circuit connection for the health comb according to the embodiment of the present invention.

As shown in FIG. 3, the semiconductor circuit 4 comprises first and second diodes D1, D2 for controlling a flow of the electric current from the electrically conductive teeth elements 3 to the touch electrodes 6, 7, and a pair of resistors R1, R2 connected respectively in parallel with the diodes D1, D2. As shown in FIG. 4, the electromagnetic device 5 comprises two permanent magnets 51 supported by the first support portions 111 of the comb casing 11, and an induction coil 52 disposed within the magnetic field of the permanent magnets 51.

Referring to FIGS. 3 and 4, the health comb according to the present invention further comprises a wire 41 connecting the electrically conductive teeth elements 3 in series, the wire 41 having first and second opposite connecting ends 411, 412. The first diode D1 of the semiconductor circuit 4 has an anode connected to the first connecting end 411 of the wire 41 and has a cathode connected to the foot-touch electrode 7 via the socket 73, the plug 72 and the wire 71. The second diode D2 of the semiconductor circuit 4 has an anode connected in series with the second connecting end 412 of the wire 41 via the electromagnetic device 5 and has a cathode connected in series with the hand-touch electrode 6. The inductive coil 52 of the electromagnetic device 5 has one end connected in series with the anode of the second diode D2 and another end connected in series with the second connecting end 412 of the wire 41.

By the foregoing construction, the comb teeth 31, the touch electrodes 6, 7, the induction coil 52, the first and second diodes D1, D2 and the resistors R1, R2 form an electrically conductive balancing circuit. The connection of the first and second diodes D1, D2 as described above allows an electric induction current to flow from the comb teeth 31 to the touch electrodes 6, 7.

The following is the operational principle of the present invention and description of use thereof. As shown in FIG. 3, when a user combs his/her hair with the health comb according to the present invention, the induction coil 52, under pressure, changes its shape along the axial direction of the induction coil 52, causing a variation of the magnetic flux and, in turn, producing within the induction coil 52 an alternative induction electromotive force (EMF). During the process of combing, the touch electrodes 6, 7 and the comb teeth 31 form a closed circuit with the user's body and, consequently, under the action of the EMF, the closed circuit produces an induction electric current. When the direction of the EMF is negative on the left side of the circuit and positive on the right side of the circuit, the electric current flows through the second diode D2, the hand-touch electrodes 6, the user's body, and the electrode portions 311 of the comb teeth 31, thereby forming a closed circuit and releasing the electricity on the head of the user. When the direction of the EMF is positive on the left side of the circuit and negative on the right side of the circuit, the electric current flows through the first diode D1, the foot-touch electrode 7, the user's body, and the electrode portions 311 of the comb teeth 31, thereby forming a closed circuit and releasing the electricity on the head of the user as well.

The connection of the first and second diodes D1, D2 in the circuit makes the EMF, no matter whether it is in the positive half circle or the negative half circle of the circuit, flow from the comb teeth 31 to the hand-touch electrodes 6 or to the foot-touch electrode 7 via outside channels, so as to effectively release the electricity on the head of the user of the health comb.

From the foregoing description, it can be seen that the present invention comprises an improved health comb for therapeutic treatment of the body of a user. It will be appreciated by those skilled in the art that obvious changes can be made to the embodiments described in the foregoing description without departing from the broad inventive concept thereof. It is understood, therefore, that this invention is not limited to the particular embodiments disclosed, but is intended to cover all obvious modifications thereof which are within the scope and the spirit of the invention as defined by the appended claims.

What I claimed is:

1. A health comb for therapeutic treatment of the body of a user, the health comb comprising:
    a comb body;
    a plurality of serially connected electrically conductive teeth elements supported by the comb body;
    at least one electrode supported by the comb body and connected to the electrically conductive teeth elements;
    electromagnetic means connected to the electrically conductive teeth elements for generating an electromotive force to produce an electric current and for directing magnetic field flux energy to a to-be-treated area of the health comb user's body; and
    a semiconductor circuit connected to the electromagnetic means and to the electrically conductive teeth elements for controlling flow of electric current from the electrically conductive teeth elements to the electrode.

2. A health comb according to claim 1; wherein the electrically conductive teeth elements, the electrode, the electromagnetic means and the semiconductor circuit are connected in series.

3. A health comb according to claim 1; wherein the semiconductor circuit comprises a diode circuit.

4. A health comb according to claim 3; wherein the diode circuit comprises a pair of diodes and a pair of resistors connected respectively in parallel with the diodes.

5. A health comb according to claim 1; wherein the electrode comprises a hand-touch electrode which is adapted to be touched by a hand of the user during use of the health comb.

6. A health comb according to claim 1; wherein the electrode comprises a foot-touch electrode which is adapted to be touched by a foot of the user during use of the health comb.

7. A health comb according to claim 6; further comprising connecting means for releasably electrically connecting the foot-touch electrode to the semiconductor circuit.

8. A health comb according to claim 7; wherein the connecting means comprises an electrical socket integral with the comb body and electrically connected to the semiconductor circuit, and an electrical plug integral with the foot-touch electrode for releasable electrical connection to the electrical socket.

9. A health comb according to claim 1; wherein the at least one electrode comprises two electrodes supported by the comb body and connected to the electrically conductive teeth elements.

10. A health comb according to claim 9; wherein one of the electrodes comprises a hand-touch electrode which is adapted to be touched by a hand of the user during use of the health comb, and the other of the electrodes comprises a foot-touch electrode which is adapted to be touched by a foot of the user during use of the health comb.

11. A health comb according to claim 10; wherein the electrically conductive teeth elements, the hand-touch electrode, the foot-touch electrode, the electromagnetic means and the semiconductor circuit are connected in series.

12. A health comb according to claim 11; further comprising a wire connecting the electrically conductive teeth elements in series, the wire having first and second opposite connecting ends; and wherein the semiconductor circuit has first and second diodes for controlling a flow of the electric current from the electrically conductive teeth elements to the hand-touch electrode and the foot-touch electrode, the first diode having an anode connected to the first connecting end of the wire and having a cathode connected to the foot-touch electrode, and the second diode having an anode connected to the second connecting end of the wire via the electromagnetic means and having a cathode connected to the hand-touch electrode.

13. A health comb according to claim 12; wherein the semiconductor circuit has a pair of resistors each respectively connected in parallel with the diodes.

14. A health comb according to claim 12; wherein the electromagnetic means comprises an inductive coil and a permanent magnet, the inductive coil having one end connected to the anode of the second diode of the semiconductor circuit and another end connected to the second connecting end of the wire.

15. A health comb according to claim 9; wherein the electrically conductive teeth elements, the electrodes, the electromagnetic means and the semiconductor circuit are connected in series.

16. A health comb according to claim 1; wherein the electromagnetic means comprises a permanent magnet and an induction coil.

17. A health comb according to claim 1; wherein the comb body comprises a first portion, a second portion integral with the first portion and a cover portion integrally connected with the first portion to define a handle portion of the comb body; and further comprising a base member integrally connected to the first portion of the comb body for supporting the electrically conductive teeth elements, the base member being comprised of insulation material.

18. A health comb according to claim 17; wherein the at least one electrode is disposed on the handle portion of the comb body.

19. A health comb according to claim 18; wherein the at least one electrode comprises a hand-touch electrode which is adapted to be touched by a hand of the user during use of the health comb.

20. A health comb according to claim 17; wherein the at least one electrode comprises two electrodes disposed on the handle portion of the comb body.

21. A health comb according to claim 20; wherein the electrodes comprise hand-touch electrodes which are adapted to be touched by a hand of the user during use of the health comb.

22. A health comb according to claim 17; wherein the at least one electrode comprises a foot-touch electrode which is adapted to be touched by a foot of the user during use of the health comb; and further comprising means for releasably electrically connecting the foot-touch electrode to the semiconductor circuit.

23. A health comb according to claim 22; wherein the connecting means comprises an electrical socket integral with the handle portion of the comb body and electrically connected to the semiconductor circuit, and an electrical plug integral with the foot-touch electrode for releasable electrical connection to the electrical socket.

24. A health comb as claimed in claim 1; wherein each of the electrically conductive teeth elements is formed of metal and has a surface coated with silver.

25. A health comb for therapeutic treatment of the body of a user, the health comb comprising:
- a comb body;
- a plurality of electrically conductive teeth elements supported by the comb body;
- a wire connecting the electrically conductive teeth elements in series, the wire having first and second opposite connecting ends;
- at least one first electrode supported by the comb body;
- a second electrode connected to the comb body;
- electromagnetic means for generating an electromotive force to produce an electric current and for directing magnetic field flux energy to a to-be-treated area of the health comb user's body; and
- a semiconductor circuit having first and second diodes for controlling flow of electric current from the electrically conductive teeth elements to the first and second electrodes, the first diode having an anode connected to the first connecting end of the wire and having a cathode connected to the second electrode, and the second diode having an anode connected to the second connecting end of the wire via the electromagnetic means and having a cathode connected to the first electrode.

26. A health comb according to claim 25; wherein the electromagnetic means comprises an inductive coil and a permanent magnet, the inductive coil having one end connected to the anode of the second diode of the semiconductor circuit and another end connected to the second connecting end of the wire.

27. A health comb according to claim 25; wherein the electrically conductive teeth elements, the first electrode, the second electrode, the electromagnetic means and the first and second diodes of the semiconductor circuit are connected in series.

28. A health comb according to claim 25; wherein the health comb is used for therapeutic treatment of the body of a user; and wherein the electromagnetic means includes means for directing magnetic field flux energy to a to-be-treated area of the health comb user's body.

29. A health comb according to claim 25; wherein the at least one first electrode comprises a hand-touch electrode which is adapted to be touched by a hand of the user during use of the health comb; and wherein the second electrode comprises a foot-touch electrode which is adapted to be touched by a foot of the user during use of the health comb.

30. A health comb according to claim 25; wherein the at least one first electrode comprises a pair of hand-touch electrodes which are adapted to be touched by a hand of the user during use of the health comb; and wherein the second electrode comprises a foot-touch electrode which is adapted to be touched by a foot of the user during use of the health comb.

31. A health comb as claimed in claim 25; wherein each of the electrically conductive teeth elements is formed of metal and has a surface coated with silver.

* * * * *